United States Patent [19]

Randall

[11] 4,199,365
[45] Apr. 22, 1980

[54] FOUNDRY COMPOSITIONS CONTAINING PROPYLENE GLYCOL MONOACETATE

[75] Inventor: George C. W. Randall, Carshalton, England

[73] Assignee: BP Chemicals Limited, London, England

[21] Appl. No.: 955,502

[22] Filed: Oct. 27, 1978

[30] Foreign Application Priority Data

Oct. 29, 1977 [GB] United Kingdom ............... 45128/77

[51] Int. Cl.$^2$ ............................................. C04B 19/04
[52] U.S. Cl. ................................... 106/84; 106/38.35; 106/289.1
[58] Field of Search .................... 106/38.35, 74, 84

[56] References Cited

U.S. PATENT DOCUMENTS

| | | | |
|---|---|---|---|
| 2,662,022 | 12/1953 | Dietz | 106/84 |
| 3,138,471 | 6/1964 | Wygant | 106/84 |
| 3,493,406 | 2/1970 | Fillet et al. | 106/74 |
| 3,607,319 | 9/1971 | Scott | 106/38.35 |
| 3,642,503 | 2/1972 | Beaney | 106/84 |
| 3,970,462 | 7/1976 | Stillman | 106/84 |

*Primary Examiner*—James Poer
*Attorney, Agent, or Firm*—Brooks, Haidt, Haffner & Delahunty

[57] ABSTRACT

The present invention relates to foundry compositions containing propylene glycol monoacetate, a silica base and a silicate. The use of propylene glycol monoacetate as ester hardeners imparts greater compressive strength to foundry cors and the strength is built up more rapidly than with conventional ester hardeners. This is believed to be due at least in part to the total miscibility of this ester with water and to the purity of the ester product.

10 Claims, No Drawings

FOUNDRY COMPOSITIONS CONTAINING PROPYLENE GLYCOL MONOACETATE

The present invention relates to the use of propylene glycol monoacetate as an organic ester hardener, especially for cold silicates used for bonding sands in the production of foundry cores.

Various hardeners may be used for hardening such silicates, the choice of a hardener being dependent upon a number of factors. These include water solubility, type of metal to be cast, type of sand used in casting, type of silicate solution, the degree of control obtainable by altering the composition and quantity of the hardener used and the toxicity and fire hazards of the hardeners used.

The most commonly used hardeners may be placed in three categories. These are:
(1) Powder hardeners such as dicalcium silicate and ferrosilicon,
(2) Carbon dioxide,
(3) Ester hardeners.

Because of the difficulties of adding powder hardeners to sodium silicate, and also of obtaining good through hardening with carbon dioxide, ester hardeners have been gaining in popularity. Ester hardeners in general have the advantages of a high rate of growth of strength and easy handling in continuous mixers. By using blends of esters it is possible to control the bench life of a formulation and obtain good through hardening. Ester hardeners are thought to operate by a combination of hydrolysis to produce hydrogen ions and dehydration of the silicate solution during this hydrolysis. However, even amongst organic esters, their degree of water solubility is important because total miscibility not only enables efficient and uniform distribution of the ester but also makes maximum use of the ester employed. In this respect conventionally used esters such as triacetin, ethylene glycol diacetate and diacetin are somewhat deficient. Triacetin is soluble in water at 20° C. to an extent of 6.7 g/100 g of water, the solubility of ethylene glycol diacetate being 16.6 g/100 g of water. Diacetin as usually produced is a mixture of mono, di and tri acetate esters of glycerol and can contain as little as 50% of the desired diacetin. The water solubility of diacetin therefore varies with the method of production and hence with the actual diacetin content of the product. Further variability is possible with diacetin depending on which two of the three hydroxyl groups of the glycerol are esterified.

It has now been found that these disadvantages may be minimised by using a composition containing a specific ester hardener.

Accordingly, the present invention is a foundry composition comprising a silica base, a silicate and propylene glycol monoacetate.

The silica base for use in such compositions is preferably sand. The desirable purity of sand would depend upon the end use of the mould produced. For example, for high quality iron and steel castings sand of very high chemical purity and high packaging density is required.

The silicate in the compositions of the present invention is suitably an alkali metal or an alkaline earth metal silicate. Sodium silicate is preferred. Of these silicates the types which have a high $SiO_2/Na_2O$ molecular ratio are preferred. Thus the silicates suitably have a $SiO_2/Na_2O$ molecular ratio of between 2:1 and 3:1, most preferably between 2.5:1 and 2.8:1. The silicates are preferably used as their aqueous solution.

The bonding reaction of sand/silicate mixtures is believed to be due to the gelation of the soluble and colloidal silica present which forms a glutinous but strongly cohesive film around the sand grains. The speed with which the gelation effect is achieved can be controlled by controlling the $SiO_2/Na_2O$ ratio, the type of sand, the water to solids ratio in the composition and the quantity of propylene glycol monoacetate used.

Propylene glycol monoacetate is totally miscible with water and hence is an extremely efficient hardening agent for silicate foundry cores. The propylene glycol monoacetate may be used as such or as a mixture thereof with other conventional hardeners such as for instance a hardener selected from diacetin, triacetin, ethylene glycol diacetate and diethylene glycol diacetate. Whether used alone or in admixture with conventional hardeners it is preferable that the ester hardening mixture contains at least 50% by weight of propylene glycol monoacetate.

Apart from the solubility aspects, propylene glycol monoacetate is superior to conventional hardeners in respect of the compressive strength imparted to the moulding and the faster rate at which such compressive strength is built up. For example, for identical concentrations, propylene glycol monoacetate imparts on an average at least twice the compressive strength to the mould when compared with diacetin.

The amount of propylene glycol monoacetate added to the silicate is suitably between 1 and 20% by weight of the silicate preferably between 5 and 15% by weight of the silicate.

The propylene glycol monoacetate used in the compositions of the present invention may be produced by conventional techniques eg by reacting in the liquid phase propylene oxide and acetic acid at an elevated temperature in the presence of a catalyst.

It is normal to use a catalyst for the reaction and many different possible catalysts would be apparent to those skilled in the art. Different catalysts produce propylene glycol monoacetate of different degrees of purity and material ranging from 59% to over 90% propylene glycol monoacetate have been prepared. However all these products are totally miscible with water and all produce higher compressive strengths and a faster rate of build up of compressive strength than diacetin. The gel time is found to vary with the propylene glycol monoacetate content, the higher the content of propylene glycol monoacetate the shorter the gel time. In general the higher propylene glycol monoacetate content material is preferred and the preferred catalyst to produce such material from propylene oxide and acetic acid is a chromium salt of saturated or unsaturated aliphatic carboxylic acid containing between 1 and 10 carbon atoms. The carboxylic acid used in preparing the chromium salt catalyst is suitably selected from formic, acetic, butyric, pentanoic, hexanoic, octanoic, 2-ethylhexanoic and decanoic acids and mixtures thereof. Whichever salt is used, it should preferably be soluble in the reaction medium. Chromium octanoate is a particularly preferred example of such a catalyst.

The chromium salt may be prepared in situ, by heating chromium hydroxide with the carboxylic acid for a short time in order to effect solution. The reaction is then continued in the usual manner. The amount of chromium salt employed in the reaction may vary between 0.1 and 5% by weight of the reactant acid employed.

A slight molar excess of propylene oxide is preferred in the reaction mixture. Thus, for example the molar ratio of propylene oxide to the reactant carboxylic acid in the reaction mixture is preferably between 1.05 and 1.2.

The reaction of the present invention may be carried out at a temperature between 40° and 120° C. The reaction pressure is preferably above atmospheric, for example between 20–40 psig. The process of the present invention may be operated batch-wise or continuously. The course of the reaction may be followed by measuring the acidity of the reaction mixture from time to time and hence determining the content of unreacted acid.

Ester hardeners including propylene glycol monoacetate need to have low levels of residual acidity eg less than 0.1% as acetic acid. Such low levels of acidity can be obtained at the reaction stage using chromium salt catalysts whilst maintaining the propylene glycol monoacetate content at around 90%. The product may be separated from the catalyst by distillation which may be carried out at reduced pressure.

When using other catalysts the reaction needs to be stopped when the acidity is at a significant level, typically around 5%, in order to maximise the content of propylene glycol monoacetate. The product then needs to be separated from the catalyst and residual acidity by fractional distillation which may be carried out under reduced pressure.

One of the significant features of this invention is that propylene glycol monoacetate thus produced has a purity of around 90% and it is this quality of the pure product which makes propylene glycol monoacetate a particularly suitable ester for use as a hardener.

The invention is further illustrated with reference to the following examples.

EXAMPLES

The gel time at room temperature was determined on the following silicate/hardener solutions. All quantities referred to are parts by weight.

| Ingredients | Comparative Test | Examples 1 | 2 | 3 |
|---|---|---|---|---|
| Sodium silicate solution (wt per ml 1.5g) | 100 | 100 | 100 | 100 |
| Diacetin | 10 | — | — | — |
| PGMA Sample 1 | — | 10 | — | — |
| PGMA Sample 2 | — | — | 10 | — |
| PGMA Sample 3 | — | — | — | 10 |

Test results are given in Table 1.

The compressive strength was assessed by monitoring the strength build-up at room temperature of silicate/sand composites. All quantities referred to are parts by weight.

The following mixes were prepared:

| Composition | Comparative Test | Examples 4 | 5 | 6 | 7 | 8 | 9 | 10 |
|---|---|---|---|---|---|---|---|---|
| New Windsor Rose Silica Sand | 100 | 100 | 100 | 100 | 100 | 100 | 100 | 100 |
| Sodium silicate solution | 3.5 | 3.5 | 3.5 | 3.5 | 3.5 | 3.5 | 3.5 | 3.5 |
| Diacetin | 0.35 | — | — | — | 0.175 | — | — | — |
| PGMA Sample 1 | — | 0.35 | — | — | — | 0.175 | — | — |
| PGMA Sample 2 | — | — | 0.35 | — | — | — | 0.175 | — |
| PGMA Sample 3 | — | — | — | 0.53 | — | — | — | 0.175 |

2 inch diameter sand briquettes were prepared by hand ramming 150 gms of sand/silicate mix. The briquettes were allowed to harden at room temperature. The compressive strength, after various times, was determined using a Howden test machine operation with a cross head speed of 1.5 inches/minute.

Test results are given in Tables 2 and 3.

In the data above and in the following Tables the expression "PGMA" refers to propylene glycol monoacetate. The references to "Samples 1, 2 and 3" indicate that samples of PGMA produced in three different batches by reacting in the liquid phase propylene oxide and acetic acid in the presence of an anion exchange resin catalyst (which was vinyl pyridine copolymerised into a cross-linked polystyrene backbone) at a temperature between 95° and 105° C. and a maximum pressure of 50 psig. The PGMA was separated from the crude product by fractional distillation.

In addition the expression "EGDA" below represents ethylene glycol diacetate.

TABLE 1

Gel Time at Room Temperature

| Example No. | Hardener at 10% on silicate | PGMA content | Gel time at 24° C. |
|---|---|---|---|
| * | Diacetin | none | 4 mins 20 secs. |
| 1 | PGMA sample 1 | 59% | 11 mins 15 secs. |
| 2 | PGMA sample 2 | 83% | 7 mins 30 secs. |
| 3 | PGMA sample 3 | 74% | 8 mins 00 secs. |

*Comparative test

TABLE 2

Compressive Strength: 10% Hardener

| Example No. | Hardener | | After 1 hour | After 3 hours | After 6 hours |
|---|---|---|---|---|---|
| * | Diacetin | | 72.6 | 64.0 | 71.7 |
| | | | 71.7 | 49.9 | 79.0 |
| | | Av. | 72.2 | 56.9 | 75.4 |
| 4 | P.G.M.A. Sample 1 | | 64.0 | 167.1 | 224.7 |
| | | | 79.5 | 124.4 | 233.8 |
| | | Av. | 71.8 | 145.8 | 229.3 |
| 5 | P.G.M.A. Sample 2 | | 61.6 | 64.0 | 113.0 |
| | | | 92.6 | 69.5 | 211.6 |
| | | Av. | 77.1 | 66.8 | 162.3 |
| 6 | P.G.M.A. Sample 3 | | 33.1 | 83.1 | 118.0 |
| | | | 42.2 | 74.9 | 134.4 |
| | | Av. | 37.2 | 79.0 | 126.0 |

*Comparative Test

TABLE 3

| Example No. and Hardener | | Compressive Strength: 5% Hardener Compressive Strength Kgs Load Plus Exposure Times | | | | | |
|---|---|---|---|---|---|---|---|
| | | After 1 hour | After 2 hours | After 3 hours | After 4 hours | After 5 hours | After 6 hours |
| *Diacetin | | 65.9 | 77.0 | 193.0 | 87.2 | 104.4 | 85.5 |
| | | 101.7 | 166.6 | 72.6 | 99.0 | 70.4 | 62.7 |
| | Av. | 78.5 | 123.0 | 133.0 | 93.1 | 87.6 | 74.0 |
| P.G.M.A. | | 91.7 | 134.8 | 174.3 | 176.6 | 159.8 | 144.8 |
| Sample 1 | | 89.4 | 151.2 | 158.9 | 140.3 | 179.8 | 151.6 |
| | Av. | 90.8 | 143.0 | 166.6 | 158.5 | 169.8 | 148.5 |
| P.G.M.A. | | 94.9 | 136.7 | 129.4 | 147.1 | 96.2 | 89.4 |
| Sample 2 | | 111.7 | 114.9 | 132.1 | 130.8 | 114.9 | 132.6 |
| | Av. | 103.5 | 125.6 | 130.8 | 138.9 | 105.8 | 111.2 |
| P.G.M.A. | | 71.3 | 122.1 | 126.7 | 122.6 | 121.2 | 145.3 |
| Sample 3 | | 69.9 | 111.2 | 176.6 | 158.9 | 113.5 | 117.6 |
| | Av. | 70.8 | 116.7 | 151.6 | 140.7 | 117.6 | 131.7 |

*Comparative test

The results set out in Tables 1 and 2 show that in sand composites a higher ultimate compressive strength was obtained with all the experimental hardeners. At both 5% and 10% additions PGMA Sample No. 1 had the fastest strength build up with the biggest ultimate strength.

EXAMPLE 10

Preparation of PGMA

To a suitable stirred, heated autoclave were charged 360 pt by weight of acetic acid and 5.4 pt by weight of chromium octanoate. The vessel was sealed and evacuated and purged with nitrogen several times to ensure removal of air. The vacuum was finally broken with nitrogen to atmospheric pressure. The vessel contents were heated to 90° C. and at this temperature the addition of 418 pt by weight (20% excess) of propylene oxide was commenced at a rate of approximately 15 pt by weight per minute. The temperature was maintained at 90°–100° C. and the maximum pressure recorded was 28 psig. After 1 hours reaction the acidity was less than 0.5%, the reactor and contents were cooled to 50° C. and vacuum applied for 30 min to remove excess propylene oxide. The crude product was distilled to give a 91% yield of a product containing 93% propylene glycol monoacetate and an acidity of 0.02% as acetic acid.

EXAMPLE 11

Comparative Gel Times and Compressive Strengths

The gel times and compressive strengths of diacetin-/EGDA mixtures were compared with a relatively inexpensive PGMA/EGDA mixture. The results are shown below.

(1) Gel times at 24° C.

| | |
|---|---|
| 60 parts Diacetin | } 10 minutes |
| 40 parts EGDA | |
| 70 parts PGMA | } 9 minutes 40 seconds |
| 30 parts EGDA | |

(2) Strengths—using 10% catalyst on silicate. The figures are kgs load to crush a 2" diameter cylindrical specimen.

| | 60/40 Diacetin/EGDA | 70/30 PGMA/EGDA |
|---|---|---|
| After 1 hour | 185 | 147 |
| After 3 hours | 238 | 299 |
| After 6 hours | 316 | 287 |

These figures indicate that the 70/30 PGMA/EGDA blend is very similar to the diacetin/EGDA blend in rate of strength build-up.

I claim:

1. A foundry composition comprising a silica base, a silicate and propylene glycol monoacetate.
2. A composition according to claim 1 wherein the silica base is sand.
3. A composition according to claims 1 wherein the silicate is an alkali metal silicate or an alkaline earth metal silicate.
4. A composition according to claim 3 wherein the silicate is sodium silicate.
5. A composition according to claim 4 wherein the silicate has a high silica to sodium oxide molecular ratio.
6. A silicate according to claim 5 wherein the silicate has a silica to sodium oxide molecular ratio between 2:1 and 3:1.
7. A composition according to claim 6 wherein the silicate has a silica to sodium oxide molecular ratio of between 2.5:1 and 2.8:1.
8. A composition according to claim 1 wherein propylene glycol monoacetate is used as a mixture thereof with a hardener selected from diacetin, triacetin, ethylene glycol diacetate and diethylene glycol diacetate.
9. A composition according to claim 8 wherein the mixture contains at least 50% by weight of propylene glycol monoacetate.
10. A composition according to claim 1 wherein the amount of propylene glycol monoacetate added to the silicate is between 1 and 20% by weight of the silicate.

* * * * *